(12) United States Patent
Kaizu et al.

(10) Patent No.: US 9,339,448 B2
(45) Date of Patent: May 17, 2016

(54) EMULSION COMPOSITION

(75) Inventors: Kazuhiro Kaizu, Yokohama (JP); Koji Yokoyama, Abiko (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/233,550

(22) PCT Filed: Aug. 8, 2012

(86) PCT No.: PCT/JP2012/070249
§ 371 (c)(1),
(2), (4) Date: Jan. 17, 2014

(87) PCT Pub. No.: WO2013/022037
PCT Pub. Date: Feb. 14, 2013

(65) Prior Publication Data
US 2014/0194522 A1    Jul. 10, 2014

(30) Foreign Application Priority Data
Aug. 9, 2011    (JP) ................................. 2011-174388

(51) Int. Cl.
| | | |
|---|---|---|
| *A61K 8/06* | (2006.01) | |
| *A61K 8/42* | (2006.01) | |
| *A61K 8/34* | (2006.01) | |
| *A61K 8/37* | (2006.01) | |
| *A61K 8/44* | (2006.01) | |
| *A61K 8/68* | (2006.01) | |
| *A61Q 19/00* | (2006.01) | |

(52) U.S. Cl.
CPC ................ *A61K 8/062* (2013.01); *A61K 8/342* (2013.01); *A61K 8/375* (2013.01); *A61K 8/42* (2013.01); *A61K 8/44* (2013.01); *A61K 8/68* (2013.01); *A61Q 19/00* (2013.01); *A61Q 19/007* (2013.01)

(58) Field of Classification Search
None
See application file for complete search history.

(56) References Cited

U.S. PATENT DOCUMENTS

| | | | | |
|---|---|---|---|---|
| 5,391,321 A | * | 2/1995 | Gruning ................ | A61K 8/066 514/941 |
| 6,001,375 A | * | 12/1999 | Lambers et al. ............. | 424/401 |
| 2003/0138466 A1 | * | 7/2003 | Bhagwat et al. ............. | 424/401 |
| 2005/0013839 A1 | * | 1/2005 | Yamamoto .................... | 424/401 |
| 2008/0268077 A1 | * | 10/2008 | Vielhaber .................... | 424/756 |
| 2009/0047309 A1 | * | 2/2009 | Maes et al. ................... | 424/401 |
| 2009/0123392 A1 | * | 5/2009 | Braun ................. | A61K 8/0208 424/47 |
| 2012/0108661 A1 | | 5/2012 | Orita et al. | |
| 2014/0004055 A1 | * | 1/2014 | Daly et al. ..................... | 424/59 |

FOREIGN PATENT DOCUMENTS

| | | |
|---|---|---|
| JP | 2001-199872 A | 7/2001 |
| JP | 2002-114631 A | 4/2002 |
| JP | 2003-012486 A | 1/2003 |
| JP | 2003-040728 A | 2/2003 |
| JP | 2004-256471 A | 9/2004 |
| JP | 2007-022997 A | 2/2007 |
| JP | 2011-016768 A | 1/2011 |
| JP | 2011-032265 A | 2/2011 |
| JP | 2012-214469 A | 11/2012 |
| WO | WO 2011004589 A1 * | 1/2011 |

OTHER PUBLICATIONS

Emalex KTG reference (2005).*
International Search Report (ISR) for PCT/JP2012/070249; I.A. fd: Aug. 8, 2012, mailed Nov. 6, 2012 from the Japanese Patent Office, Tokyo, Japan.
International Preliminary Report on Patentability (IPRP), Chapter I of the Patent Cooperation Treaty, including the Written Opinion for PCT/JP2012/070249; I.A. fd: Aug. 8, 2012, issued Feb. 11, 2014, by the International Bureau of WIPO, Geneva, Switzerland.

* cited by examiner

*Primary Examiner* — Robert A Wax
*Assistant Examiner* — Caralynne Helm
(74) *Attorney, Agent, or Firm* — Sterne, Kessler, Goldstein & Fox P.L.L.C.

(57) ABSTRACT

Provided is an emulsion composition comprising the following ingredients (A), (B), (C), (D), (E), and (F):
(A) glyceryl monofatty acid ester derived from a linear-chain fatty acid having 10 to 24 carbon atoms;
(B) a higher alcohol having 10 to 24 carbon atoms;
(C) a ceramide;
(D) an anionic surfactant;
(E) a polar oil selected from branched fatty acid esters having an IOB of from 0.2 to 0.85 and having a hydroxyl group or an amino group; and
(F) water,
wherein the mass ratio of the total content of ingredients (A), (B), and (C) and ingredient (D) in terms of acid to the content of ingredient (E), ((A)+(B)+(C)+(D))/(E), is from 1.2 to 25.

10 Claims, No Drawings

EMULSION COMPOSITION

FIELD OF THE INVENTION

The present invention relates to an emulsion composition.

BACKGROUND OF THE INVENTION

α-Gel has a hydrate-type crystal structure, which is a lamellar structure. The intercorneocytic lipid present in the horny layer (i.e., the outermost skin layer) generally has the α-gel structure. The horny layer prevents entry of outside substances into the skin as well as transepidermal water loss. Also, the layer retains water, whereby the softness and smooth appearance of the skin can be maintained. It has been known that, in the skin, the horny layer retains water as bound water in an amount of about 33% by mass, and intercorneocytic lipid retains about 13% by mass of the bound water.

Since the α-gel can thus retain water, it, is investigated for application to, for example, cosmetics.

For example, Patent Document 1 describes that an emulsion composition containing a ceramide, a glyceryl monofatty acid ester, a higher alcohol, and other ingredients forms an α-gel structure. Since this emulsion composition stably contains the ceramide and has an excellent moisturizing effect, but it gives friction feeling, however, an emulsion composition giving further satisfactory feeling in use has been demanded.

CITATION LIST

Patent Documents

Patent Document 1: JP-A-2007-22997

SUMMARY OF THE INVENTION

The present invention provides an emulsion composition comprising the following ingredients (A), (B), (C), (D), (E), and (F):

(A) a glyceryl monofatty acid ester derived from a linear-chain fatty acid having 10 to 24 carbon atoms;
(B) a higher alcohol having 10 to 24 carbon atoms;
(C) a ceramide;
(D) an anionic surfactant;
(E) a polar oil selected from branched fatty acid esters having an IOB of from 0.2 to 0.85 and having a hydroxyl group or an amino group; and
(F) water,
wherein, a mass ratio of the total content of ingredients (A), (B), and (C) and ingredient (D) in terms of acid to the content of ingredient (E), ((A)+(B)+(C)+(D))/(E), is from 1.2 to 25.

DETAILED DESCRIPTION OF THE INVENTION

The present invention relates to an emulsion composition stably containing a ceramide, having an excellent moisturizing effect, and also giving reduced friction feeling to provide excellent feeling in use.

The present inventors have found that an emulsion composition further softening the α-gel film which is formed during the application and after the application of the composition and giving reduced friction feeling to provide excellent feeling in use can be obtained by using a specific branched polar oil at a specific ratio relative to the α-gel designed so as to enhance the water retention capability.

The emulsion composition of the present invention forms an α-gel structure to prevent crystallization of the ceramide and thereby stably contains the ceramide, has an excellent moisturizing effect, and also gives reduced friction feeling to provide excellent feeling in use.

In the present invention, the term "friction feeling" refers to a feel, in formation of a film coating of an emulsion composition by applying the composition to the skin with the fingers slide, such that the fingers are difficult to slide on the skin and the movement of the fingers is stopped, and the term "giving reduced friction feeling" refers to that in application of an emulsion composition to the skin, the emulsion composition has appropriate slipperiness and smoothness while maintaining a protective function of covering the skin not to give an occlusive feel.

Examples of ingredient (A), the glyceryl monofatty acid ester derived from a linear-chain fatty acid having 10 to 24 carbon atoms, employed in the present invention include glyceryl monolaurate, glyceryl monomyristate, glyceryl monopalmitate, glyceryl monostearate, glyceryl monobehenate, glyceryl monooleate, and the like.

Among them, glyceryl monofatty acid esters derived from a linear-chain fatty acid having 18 to 22 carbon atoms are preferred, and glyceryl monopalmitate, glyceryl monostearate, and glyceryl monobehenate are more preferred.

The glyceryl monofatty acid esters as ingredient (A) may be used alone or in combination of two or more. From the viewpoint of enhancing water retention capability, the content of ingredient (A) in the emulsion composition of the present invention is preferably 0.001% by mass or more, more preferably 0.05% by mass or more, even more preferably 0.1% by mass or more and preferably 10% by mass or less, more preferably 3% by mass or less, even more preferably 2% by mass or less. Furthermore, the content of ingredient (A) in the emulsion composition of the present invention is preferably from 0.001% to 10% by mass, more preferably from 0.05% to 3% by mass, and even more preferably from 0.1% to 2% by mass.

The higher alcohol employed as ingredient (B) in the present invention has 10 to 24 carbon atoms, and examples thereof include lauryl alcohol, myristyl alcohol, cetanol, stearyl alcohol, behenyl alcohol, oleyl alcohol, and the like.

Among them, higher alcohols having 14 to 22 carbon atoms are preferred, and cetanol, stearyl alcohol, and behenyl alcohol are more preferred.

The higher alcohols as ingredient (B) may be used alone or in combination of two or more. From the viewpoint of enhancing water retention, the content of ingredient (B) in the emulsion composition of the present invention is preferably 0.001% by mass or more, more preferably 0.1% by mass or more, even more preferably 0.5% by mass or more and preferably 10% by mass or less, more preferably 3% by mass or less, even more preferably 2.5% by mass or less. Furthermore, the content of ingredient (B) in the emulsion composition of the present invention is preferably from 0.001% to 10% by mass, more preferably from 0.1% to 3% by mass, and even more preferably from 0.5% to 2.5% by mass.

The ceramide as ingredient (C) is preferably a naturally occurring ceramide (I) shown below and/or a pseudo-ceramide (II). Specifically, the naturally occurring ceramide (I) is preferably a ceramide represented by the following formula (1), and the pseudo-ceramide (II) is preferably a ceramide represented by the following formula (2). A layered lamellar structure can be formed by the ceramide having a structure represented by formula (1) or (2) and being mixed with ingredients (A), (B), and (D).

Naturally occurring ceramide (I) represented by formula (1) or a synthetic product having the same structure and derivatives thereof (hereinafter, referred to as natural-type ceramide):

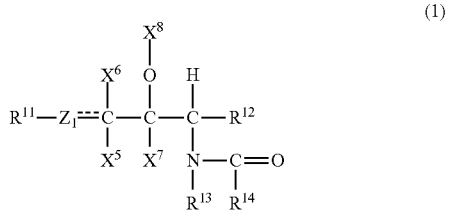

(1)

(wherein $R^{11}$ represents a C7 to C19 linear-chain, branched-chain or cyclic, and saturated or unsaturated hydrocarbon group which is optionally substituted by a hydroxyl group; $Z_1$ represents a methylene group or a methine group; each of $X^5$, $X^6$, and $X^7$ independently represents a hydrogen atom, a hydroxyl group, or an acetoxy group; $X^8$ represents a hydrogen atom, or forms an oxo group together with the adjacent oxygen atom (with the proviso that when $Z_1$ is a methine group, then one of $X^5$ and $X^6$ is a hydrogen atom, and the other is absent, and when $X^8$ forms an oxo group, then $X^7$ is absent); $R^{12}$ represents a hydroxymethyl group or an acetoxymethyl group; $R^{13}$ represents a hydrogen atom or a C1 to C4 alkyl group; $R^{14}$ represents a C5 to C30 linear-chain, branched-chain or cyclic, and saturated or unsaturated hydrocarbon group which is optionally substituted by a hydroxyl group, or such an alkyl group to which a C8 to C22 linear-chain or branched-chain, and saturated or unsaturated fatty acid which is optionally substituted by a hydroxyl group is bonded at the ω-end via ester bonding; and the broken line indicates that a bond between C and $Z_1$ represents an optional unsaturated bond).

As the preferred ingredient (C), $R^{11}$ is a C7 to C19 (more preferably C13 to C15) linear-chain alkyl group; $R^{14}$ is a C9 to C27 linear-chain alkyl group which is optionally substituted by a hydroxyl group, or a C9 to C27 linear-chain alkyl group to which linoleic acid is bonded via ester bonding. Preferably, $X^8$ represents a hydrogen atom or forms an oxo group together with an oxygen atom. $R^{14}$ is preferably a tricosyl group, a 1-hydroxypentadecyl group, a 1-hydroxytricosyl group, a heptadecyl group, a 1-hydroxyundecyl group, or a nonacosyl group to which linoleic acid is bonded at the ω-position via ester bonding.

Specific examples of the natural-type ceramide include ceramide Types 1 to 7 in which sphingosine, dihydrosphingosine, phytosphingosine, or sphingadienine is amidated (for example, ceramides of pig and human described in FIG. 2 of J. Lipid Res., 24: 759 (1983), and FIG. 4 of J. Lipid. Res., 35: 2069 (1994)).

The ceramides also encompass N-alkyl forms (e.g., methyl form) thereof.

Regarding these ceramides, either a natural-type optically active form (D(−) form) or a non-natural-type optically active form (L(+) form) may be used. Furthermore, a mixture of a natural-type form and a non-natural-type form may also be used. The configuration of the aforementioned compound may be of natural-type, of non-natural-type, or of mixed type. Among them, preferred are compounds: CERAMIDE 1, CERAMIDE 2, CERAMIDE 3, CERAMIDE 5, CERAMIDE 6II, (INCI, 8th Edition), and those represented by the following formulas.

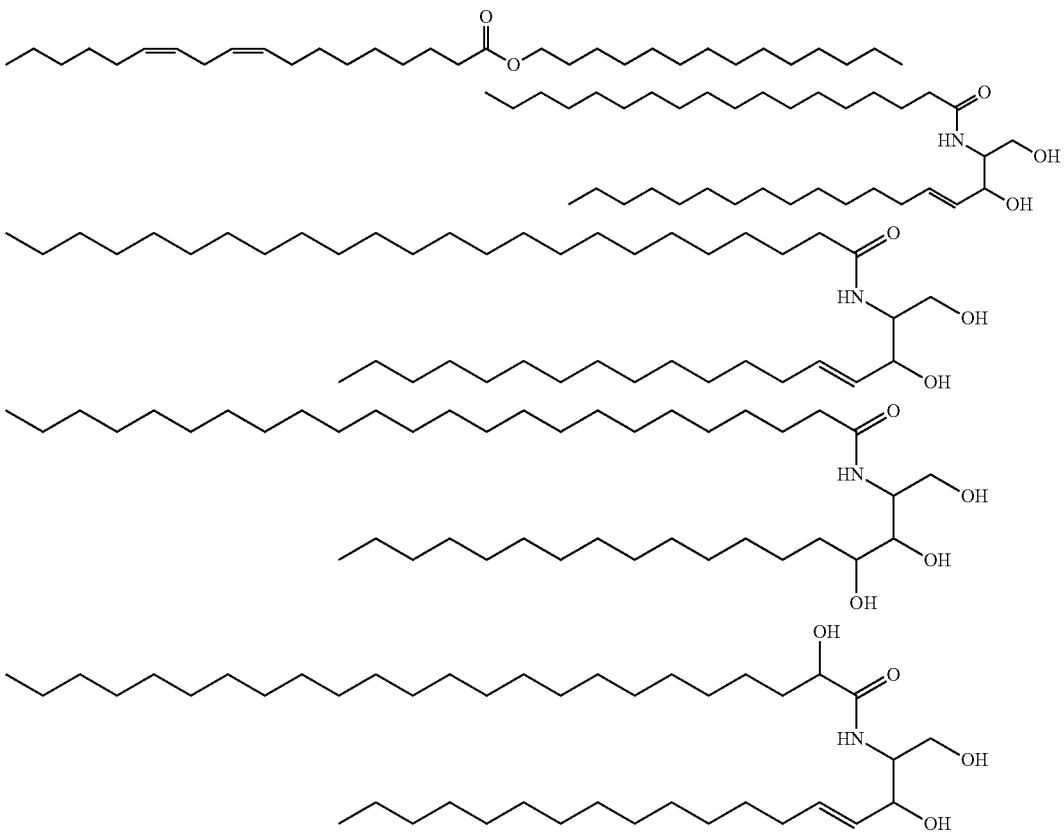

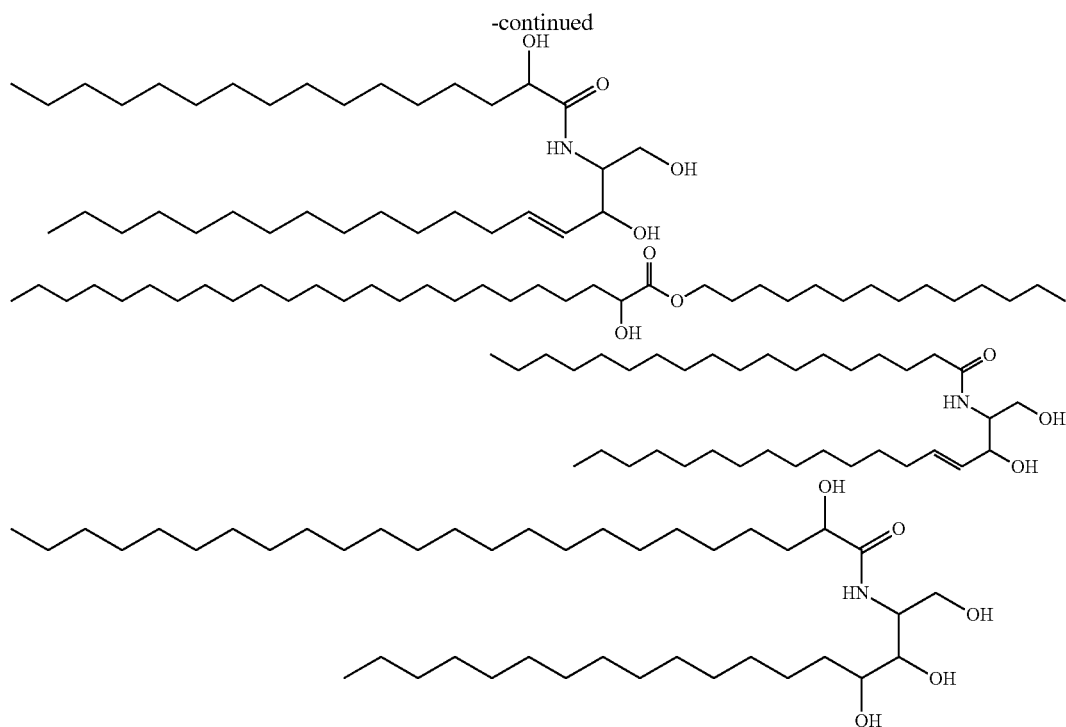

These ceramides may be natural extracts and/or synthetic products. Commercial products thereof may also be employed in the invention.

Examples of such natural-type ceramide commercial products include Ceramide I, Ceramide III, Ceramide IIIA, Ceramide IIIB, Ceramide IIIC, and Ceramide VI (COSMOFERM); Ceramide TIC-001 (Takasago International Corporation); CERAMIDE II (Quest International); DS-Ceramide VI, DS-CLA-Phytoceramide, C6-Phytoceramide, and DS-ceramide Y3S (DOOSAN); and CERAMIDE 2 (Sederma),

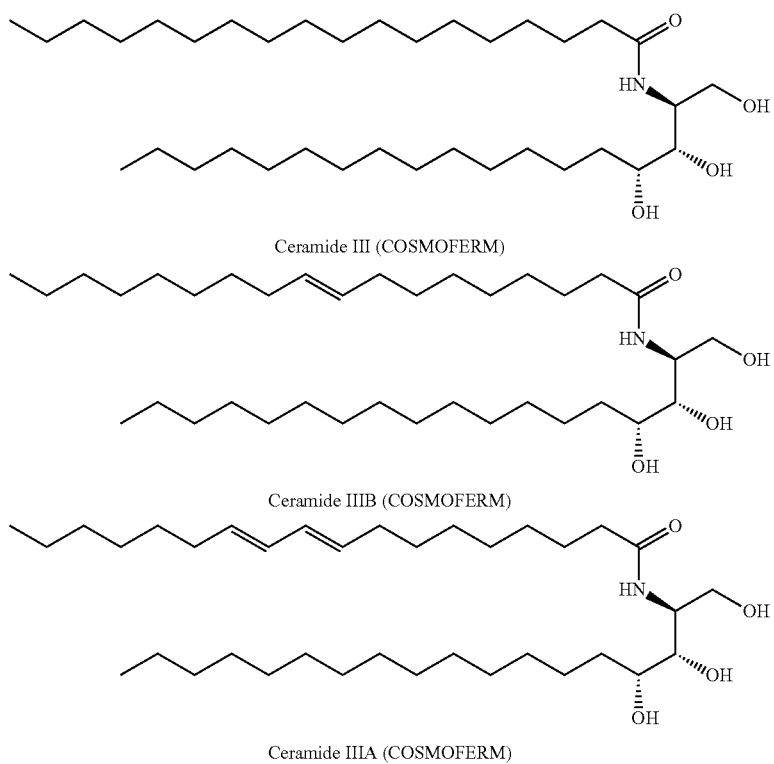

-continued
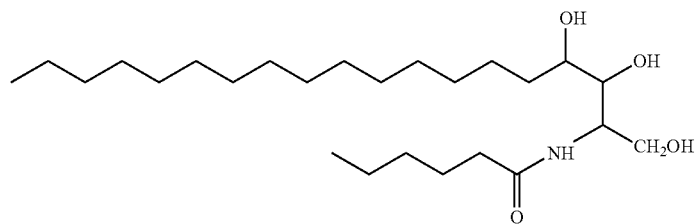
Phytoceramide (DOOSAN)
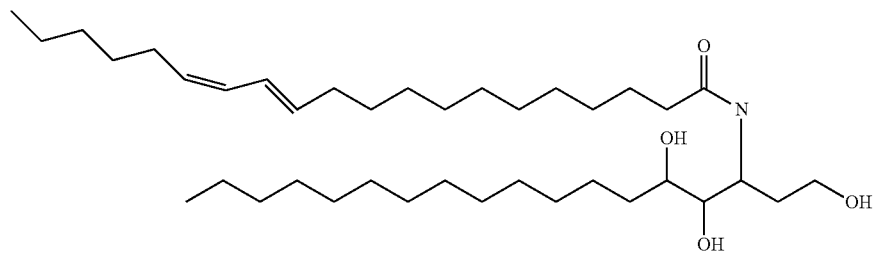
DS-CLA-Phytoceramide (DOOSAN)
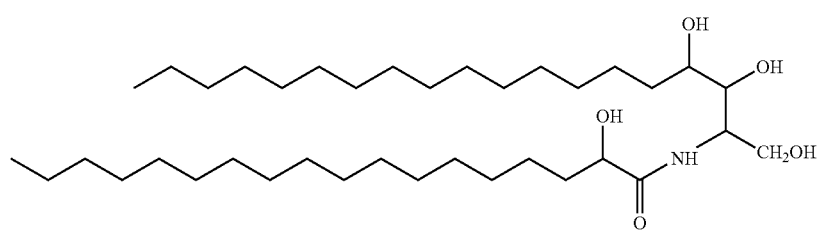
DS-Ceramide VI (DOOSAN)
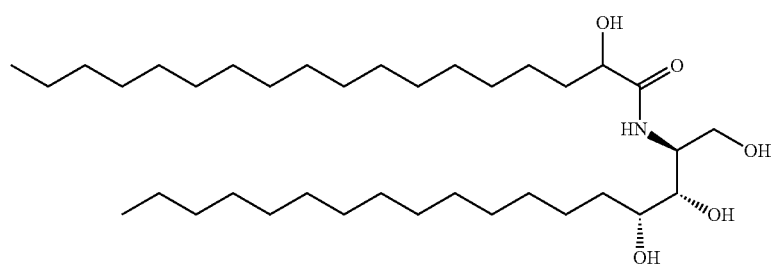
Ceramide VI (COSMOFERM)
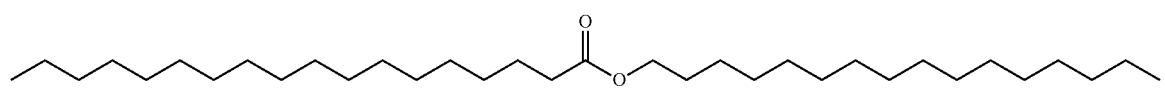
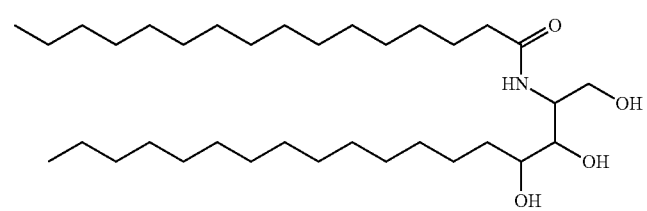
Ceramide I (COSMOFERM)

(II): Pseudo-ceramides represented by formula (2)

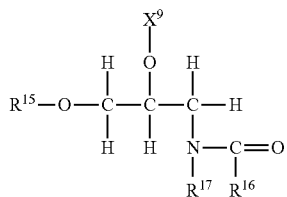

(wherein $R^{15}$ represents a hydrogen atom or a C10 to C22 linear-chain, branched-chain, or cyclic, and saturated or unsaturated hydrocarbyl group which is optionally substituted by a hydroxyl group; $X^9$ represents a hydrogen atom, an acetyl group, or a glyceryl group; $R^{16}$ represents a C5 to C22 linear-chain, branched-chain cyclic, and saturated or unsaturated hydrocarbon group which is optionally substituted by a hydroxyl group or amino group, or such a hydrocarbon group to which a C8 to C22 linear-chain or branched-chain, and saturated or unsaturated fatty acid which is optionally substituted by a hydroxyl group is bonded at the ω-end via ester bonding; and $R^{17}$ represents a hydrogen atom or an alkyl group optionally substituted by a hydroxyl group, a hydroxyalkoxy group, an alkoxy group, or an acetoxy group and such an alkyl group has 1 to 30 carbon atoms in total).

$R^{16}$ is preferably a nonyl group, a tridecyl group, a pentadecyl group, an undecyl group to which linoleic acid is bonded at the ω-position thereof via ester bonding, pentadecyl group to which linoleic acid is bonded at the ω-position thereof via ester bonding, a pentadecyl group to which 12-hydroxystearic acid is bonded, at the ω-position thereof via ester bonding, or an undecyl group to which methyl-branched isostearic acid is bonded at the ω-position thereof via amido bonding.

When $R^{15}$ is a hydrogen atom, $R^{17}$ is an alkyl group optionally substituted by a hydroxyl group, hydroxyalkoxy group, an alkoxy group, or an acetoxy group and such an alkyl group has 10 to 30 (preferably 12 to 20) carbon atoms in total. When $R^{15}$ is a C10 to C22 linear-chain, branched-chain, or cyclic, and saturated or unsaturated hydrocarbon group which is optionally substituted by a hydroxyl group, $R^{17}$ resents preferably a hydrogen atom or an alkyl group optionally substituted by a hydroxyl group, a hydroxyalkoxy group, an alkoxy group, or an acetoxy group and such an alkyl group has 1 to 8 carbon atoms in total. The hydroxyalkoxy or alkoxy group in $R^{17}$ preferably has 1 to 7 carbon atoms.

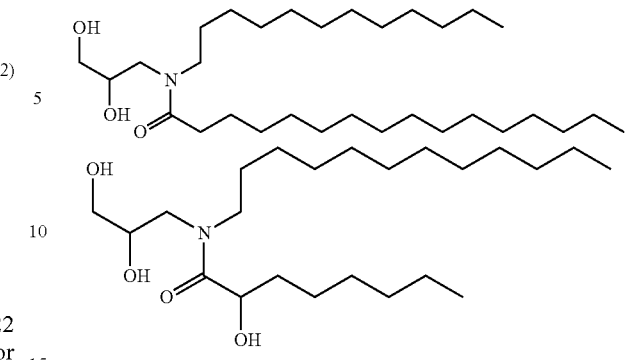

Preferred pseudo-ceramides represented by formula (2) are the case where $R^{15}$ is a hexadecyl group, $X^9$ is a hydrogen atom, $R^{16}$ is a pentadecyl group, and $R^{17}$ is a hydroxyethyl group; the case where $R^{15}$ is a hexadecyl group, $X^9$ is a hydrogen atom, $R^{16}$ is a nonyl group, and $R^{17}$ is a hydroxyethyl group. More preferred pseudo-ceramides represented by formula (2) are the case where $R^{15}$ is a hexadecyl group, $X^9$ is a hydrogen atom, $R^{16}$ is a pentadecyl group, and $R^{17}$ is a hydroxyethyl group (i.e., N-(hexadecyloxyhydroxypropyl)-N-hydroxyethylhexadecanamide).

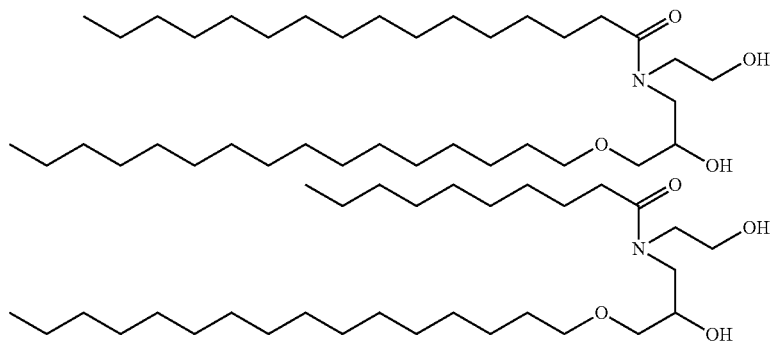

The ceramides as ingredient (C) may be used alone or in combination of two or more. From the viewpoint of allowing ingredient (C) to sufficiently permeate the skin, the content of ingredient (C) in the emulsion composition of the present invention is preferably 0.001% by mass or more, more preferably 0.1% by mass or more, even more preferably 0.2% by mass or more and preferably 10% by mass or less, more preferably 5% by mass or less, even more preferably 3% by mass or less. Furthermore, the content of ingredient (C) in the emulsion composition of the present invention is preferably from 0.001% to 10% by mass, and from the viewpoint of balancing the skin permeation with the reduction in friction feeling, the content is more preferably from 0.1% to 5% by mass, and even more preferably from 0.2% to 3% by mass.

Examples of the anionic surfactant of ingredient (D) used in the present invention include fatty acid salts derived from fatty acids having 12 to 24 carbon atoms such as sodium laurate, potassium palmitate, and arginine stearate; alkyl sulfate ester salts such as sodium lauryl sulfate and potassium lauryl sulfate; alkyl ether sulfate ester salts such as polyoxyethylene lauryl sulfate triethanolamine salt; N-acylsarcosine salts such as lauroyl sarcosine sodium salt; fatty acid amidosulfonate salts such as N-stearoyl-N-methyltaurine sodium salt and N-myristoyl-N-methyltaurine sodium salt; alkyl phosphate salts such as sodium monostearyl phosphate; polyoxyethylene alkyl ether phosphate ester salts such as sodium polyoxyethylene oleyl ether phosphate and sodium polyoxyethylene stearyl ether phosphate; long-chain sulfosuccinate salts such as sodium di-2-ethylhexylsulfosuccinate; and long-chain N-acylglutamate salts such as monosodium N-lauroyl-glutamate, sodium N-stearoyl-L-glutamate, arginine N-stearoyl-L-glutamate, sodium N-stearoylglutamate, and sodium N-myristoyl-L-glutamate.

Among them, fatty acid salts derived from fatty acids having 12 to 24 carbon atoms, fatty acid amidosulfonates derived from fatty acids having 14 to 22 carbon atoms, polyoxyethylene alkyl ether phosphates having C14-C22 alkyl groups, and N-acylglutamates derived from fatty acids having 12 to 22 carbon atoms are preferred, and sodium salts and arginine salts are preferred salts. Furthermore, fatty acid amidosulfonates derived from fatty acids having 18 to 22 carbon atoms, polyoxyethylene alkyl ether phosphates having C18-C22 alkyl groups, and N-acylglutamates derived from fatty acids having 18 to 22 carbon atoms are more preferred; and one or more selected from sodium N-stearoyl-N-methyltaurine, arginine N-stearoyl-L-glutamate, and sodium polyoxyethylene stearyl ether phosphate are even more preferred.

The anionic surfactants as ingredient (D) may be used alone or in combination of two or more. From the viewpoint of reducing crystallization of ingredient (C), the content of ingredient (D), in terms of acid, in, the emulsion composition of the present invention is preferably 0.01% by mass or more, more preferably 0.05% by mass or more, even more preferably 0.1% by mass or more and preferably 3% by mass or less, more preferably 2% by mass or less, even more preferably 1.5% by mass or less. Furthermore, the content of ingredient (D), in terms of acid, in the emulsion composition of the present invention is preferably from 0.01% to 3% by mass, more preferably from 0.05% to 2% by mass, and even more preferably from 0.1% to 1.5% by mass.

Note that ingredient (D) is a compound obtained by neutralization of an acid compound with a base and that the content of ingredient (D) is the content as the acid compound or the content in terms of the acid.

The polar oil selected from branched fatty acid esters employed in the present invention as ingredient (E) has an IOB of from 0.2 to 0.85, and from the viewpoints of reducing friction feeling and improving feeling in use, the polar oil more preferably has an IOB of from 0.25 to 0.60 and even more preferably from 0.28 to 0.5. Note that ingredient (E) includes those classified as oil and those classified as oil and nonionic surfactants.

Here, the IOB indicates the ratio (inorganic organic balance) of an inorganic value to an organic value determined based on an organic conceptual diagram (Atsushi Fujita, Estimation of organic compound and organic conceptual diagram (Yuki kagobutsu no yosoku to yuki gainen zu), Kagaku no Ryoiki, Vol. 11, No. 10, (1957), 719-725) and can be calculated by the following expression:

$$IOB\ value = \frac{inorganic\ value}{organic\ value}$$

The branched fatty acid ester of ingredient (E) is a polar oil selected from branched fatty acid esters having hydroxyl groups and branched fatty acids having amino groups. The branched fatty acid ester may have a polyol as the alcohol portion or a polyvalent fatty acid as the fatty acid. The amino group may be converted into an amide bond.

Specific examples of the branched fatty acid esters include branched fatty acid esters having hydroxyl groups such as octyldodecyl lactate (IOB=0.36), difatty acid glyceryl ester (IOB=0.32) composed of isostearic acid and myristic acid, diglyceryl diisostearate (IOB=0.42), erythrityl triethylhexanoate (IOB=0.55) and diglyceryl monoisostearate (IOB=0.81); and branched fatty acid esters having amide bonds, such as di(cholesteryl/octyldodecyl)N-lauroyl-L-glutamate (IOB=0.29 to 0.35).

Among them, one or more branched fatty acid esters selected from branched fatty acid esters having hydroxyl groups and branched fatty acid esters having amide bonds are preferred, and a polar oil composed of one or more branched fatty acid esters selected from octyldodecyl lactate (IOB=0.36), difatty acid glyceryl ester (IOB=0.32) composed of isostearic acid and myristic acid, diglyceryl diisostearate (IOB=0.42), and di(cholesteryl/octyldodecyl)N-lauroyl-L-glutamate (IOB=0.29 to 0.35) is more preferred.

The polar oils as ingredient (E) may be used alone or in combination of two or more. From the viewpoints of preventing crystallization of ingredient (C) and reducing friction feeling, the content of ingredient (E) in the emulsion composition of the present invention is preferably 0.001% by mass or more, more preferably 0.15% by mass or more, even more preferably 0.2% by mass or more and preferably 5% by mass or less, more preferably 4% by mass or less, even more preferably 3% by mass or less. Furthermore, the content of ingredient (E) in the emulsion composition of the present invention is preferably from 0.001% to 5% by mass, more preferably from 0.15% to 4% by mass, and still more preferably from 0.2% to 3% by mass.

In the present invention, the mass ratio, ((A)+(B)+(C)+(D))/(E), of the total content of ingredients (A), (B), and (C) and ingredient (D) in terms of acid to the content, of ingredient (E) is from 1.2 to 25. Furthermore, from the viewpoints of preventing crystallization of ingredient (C) to improve stability and of reducing friction feeling, the ratio is preferably from 1.25 to 20 and more preferably from 1.5 to 17.

In addition, the mass ratio (B/C) of the content of ingredient (B) to the content of ingredient (C) is preferably from 0.2 to 5, more preferably from 0.25 to 4, and even more preferably from 0.3 to 4, from the viewpoints of preventing crystallization of ingredient (C) to improve stability and of reducing friction feeling.

The mass ratio (D/E) of the content of ingredient (D) in terms of acid to the content of ingredient (E) is preferably from 0.1 to 5, more preferably from 0.15 to 4, and even more preferably from 0.2 to 3, from the viewpoints of preventing crystallization of ingredient (C) to improve stability and of reducing friction feeling.

In the present invention, the emulsion composition of the present invention preferably contains an ingredient (F) (i.e., water) in an amount of from 20 to 99% by mass, more preferably from 40 to 90% by mass.

The composition of the invention may further comprise other aqueous base materials, for example, a C1 to C4 lower alcohol such as ethanol and propanol.

The emulsion composition of the present invention preferably further comprises a polyol (G) having an IOB of from 1.5 to 3.5, from the viewpoint of further reducing friction feeling.

Specific examples of the polyol include linear-chain or branched-chain glycol, monoalkyl mono, di, or trialkyl glycol ether, polyethylene glycol, polypropylene glycol, polyoxyethylene glycol, and the like. More specifically, examples of the polyol include glycols having 2 to 10 carbon atoms such as 1,3-butylene glycol (IOB=2.50), isoprene glycol (IOB=2.0), propylene glycol (IOB=3.33), 1,3-propanediol (IOB=3.33), and dipropylene glycol (IOB=1.83); and diethylene glycol monoethyl ether (IOB=1.6), polypropylene glycol having a molecular weight of from 100 to 10000, polyethylene glycol having a molecular weight of 100 to 10000, and polyoxyethylene diglyceryl ether having an average addition molar number of the oxyethylene of from 4 to 20.

The polyols as ingredient (G) may be used alone or in combination of two or more. From the viewpoint of further reducing friction feeling, the content of ingredient (G) in the emulsion composition of the present invention is preferably 0.001% by mass or more, more preferably 0.2% by mass or more, even more preferably 2% by mass or more and preferably 20% by mass or less, more preferably 15% by mass or less, even more preferably 10% by mass or less. Furthermore, the content of ingredient (G) in the emulsion composition of the present invention is preferably from 0.001% to 20% by mass, more preferably from 0.2% to 20% by mass, even more preferably from 2% to 20% by mass. Furthermore, from the viewpoint of improving moist feeling while preventing stickiness feeling, the content is preferably from 0.2% to 15% by mass and more preferably from 2% to 10% by mass.

In the case of containing ingredient (G), the mass ratio, $((A)+(B)+(C)+(D))/(G)$, of the total content of ingredients (A), (B), and (C) and ingredient (D) in terms of acid to the content of ingredient (G) is preferably from 0.1 to 20, more preferably from 0.2 to 15, and even more preferably from 0.22 to 3, from the viewpoint of preventing stickiness while further reducing friction feeling.

The emulsion composition of the present invention may further comprise an oil other than ingredients (B), (C), and (E). Examples of the oil include hydrocarbon oils such as liquid paraffin, hydrogenated polyisobutene, hydrogenated polydecene, squalane, and petrolatum; higher fatty acids such as stearic acid, behenic acid, and isomyristic acid; vegetable oil such as olive oil and jojoba oil; silicone oils such as dimethylpolysiloxane(methylpolysiloxane), cyclic dimethylpolysiloxane, methylphenylpolysiloxane, amino-modified silicone, carboxy-modified silicone, alcohol-modified silicone, alkyl-modified silicone, polyether-modified silicone, and fluorine-modified silicone; and fluorine-containing oils such as perfluoroalkylethylphosphoric acid, perfluoroalkylpolyoxyethylenephosphoric acid, perfluoropolyether, and polytetrafluoroethylene. The emulsion composition of the present invention can further comprise a polar oil other than ingredient (E), such as neopentyl glycol dicaprate.

Such an oil is preferably not contained in the emulsion composition of the present invention or contained in an amount of 20% by mass or less and is more preferably contained in an amount of 15% by mass or less. The content of the polar oil having an IOB of 0.2 or more, other than ingredient (E), such as neopentyl glycol dicaprate, is preferably 5% by mass or less, and the content of the oil having an IOB of from 0.1 to 0.2, such as olive oil, is preferably 5% by mass or less.

The emulsion composition of the present invention may further comprise active ingredients or additives which are employed in typical cosmetics within a range of not inhibiting the effect of the present invention. Examples of such ingredients and additives include water-soluble vitamins such as ascorbic acid, nicotinamide, and nicotinic acid; animal and vegetable extracts such as Phellodendoron Amurense extract, licorice extract, aloe extract, horsetail extract, tea extract, cucumber extract, clove extract, ginseng extract, witch hazel extract, placenta extract, seaweed extract, horse chestnut extract, chamomilla recutita extract, Japanese citron (Yuzu) extract, false-arborvitae tree extract, althaea officinalis extract, royal jelly extract, eucalyptus extract, brown algae extract, and false-arborvitae tree extract; bases such as potassium hydroxide, sodium hydroxide, triethanolamine, and sodium carbonate; acids such as citric acid, tartaric acid, lactic acid, phosphoric acid, succinic acid, and adipic acid; and thickening agents such as carboxyvinyl polymer, sodium arginate, carrageenan, carboxymethylcellulose, hydroxyethylcellulose, guar gum, xanthan gum, carboxymethylchitosan, sodium hyaluronate, oxazoline-modified silicone, N,N-dimethylaminoethyl methacrylate diethylsulfate salt-N,N-dimethylacrylamide-polyethylene glycol dimethacrylate copolymer.

The emulsion composition of the present invention can be obtained as an O/W emulsion composition by, for example, any of the following production methods (1) to (3):

Process (1) comprising a step of heating and stirring a first oil phase containing ingredients (A), (B), and (C) at 80° C. to 90° C. for mixing them, then a step of adding a first water phase containing the acid compound of ingredient (D), a base and a part of ingredient (F) heated to 80° C. to 90° C. to the first oil phase, then a step of adding a second oil phase that is a mixture of ingredient (E) and other oily ingredients heated to 80° C. to 90° C. to the resulting mixture and stirring them, and a step of cooling the mixture to 40° C. to 25° C. with stirring and adding the remaining ingredient (F) and other water-soluble ingredients (second water phase) to the cooled mixture with stirring;

Process (2) comprising a step of heating and stirring a first oil phase containing ingredients (A), (B), and (C) and the acid compound of ingredient (D) at 80° C. to 90° C. for mixing them, then a step of adding a first water phase containing a base for neutralizing ingredient (D) and a part of water as ingredient (F) heated to 80° C. to 90° C. to the first oil phase and mixing them, then a step of mixing the mixture with ingredient (E) and other oily ingredients (second oil phase) heated to 80° C. to 90° C., and a step of cooling the mixture to 40° C. to 25° C. with stirring and adding the remaining ingredient (F) and other water-soluble ingredients (second water phase) to the cooled mixture with stirring; and Process (3) comprising a step of heating and stirring a first oil phase containing, ingredients (A), (B), and (C) and a part of the acid compound of ingredient (D) at 80° C. to 90° C. for mixing them, then a step of adding a first water phase containing the remaining acid compound of ingredient (D), a base and a part of ingredient (F) heated to 80° C. to 90° C. to the first oil phase and mixing them with stirring, then a step of mixing the mixture with ingredient (E) and other oily ingredients (second oil phase) heated to 80° C. to 90° C. with stirring, and a step of cooling the mixture to 40° C. to 25° C. with stirring, then adding the remaining ingredient (F) and other water-soluble ingredients (second water phase) to the cooled mixture with stirring.

In the production methods (1) to (3), the cooling may be cooling to a room temperature of 40° C. or less, more preferably 30° C. or less, and more preferably 15° C. or more, even more preferably 20° C. or more.

As described above, from the viewpoint of manufacturability and stability of the composition of the present invention, the production method preferably includes a step of heating and mixing ingredients (A) to (D) before the step of adding and mixing ingredient (E) and preferably includes a step of neutralizing the acid compound of ingredient (D) with a base before the step of adding and mixing ingredient (E).

In the above-mentioned production methods, from the viewpoint of productivity and stability over time, production methods (1) and (2) are preferred, and production method (1) is more preferred. The amount of ingredient (F) first water phase production method (1) or (2) is preferably from 10% to 50% by mass, more preferably from 15% to 45% by mass, based on the total amount of the produced emulsion composition, and the amount of ingredient (F) in the first water phase may be an amount that allows neutralization of the acid compound of ingredient (D) with a base to give a solution state.

The thus-produced emulsion composition assumes α-gel (α-type crystal), with deposition of γ-type crystals being prevented. α-Gel can be identified through structure analysis by wide-angle X-ray diffraction (Bragg angle: 21° to 23°). α-Type structure is a hexagonal crystal structure type, in which an oleophilic group is arranged perpendicular to the hydrophilic group layer, with one characteristic diffraction peak at a Bragg angle of around 21 to 23°.

Furthermore, ingredients (A) to (D) form layered, lamellae, and peaks can be confirmed at a ratio of Bragg angles of 1:2:3:4 by small-angle X-ray diffraction (Bragg angle: 0.3° to 5°). The emulsion composition of the present invention is concentrated with a centrifuge and is subjected to measurement by small-angle X-ray diffraction. As described above, it is believed that in the emulsion composition of the present invention, the continuous phase is a water phase, and appropriate flexibility is imparted to the α-gel or layered lamellar structure formed from ingredients (A) to (D) by mixing with ingredient (E), and as a result, friction feeling is reduced.

The layered lamellae formed from ingredients (A) to (D) have a structure in which hydrophobic portions and hydrophilic portions are stacked in a layer. When ingredient (E) is a branched fatty acid having a hydroxyl group, it is believed that the branched fatty acid ester is apt to be incorporated into the lamellar structures and thereby that the fatty acid site of the hydrophobic portion infiltrates into the hydrophobic portion of the layered lamellae to loosen the lamellar structure. When ingredient (E) is a branched fatty acid ester having an amino group, it is believed that the ester is apt to be incorporated into the lamellar structure because of the presence of the amino group and thereby that the fatty acid site of the hydrophobic portion infiltrates into the hydrophobic portion of the layered lamellae to loosen the lamellar structure.

In the present invention, α-gel is formed to give a layered lamellar structure, even if ingredient (E) is contained. Consequently, an emulsion composition giving reduced friction feeling and, thereby having satisfactory smoothness and slipperiness while maintaining a moisturizing effect (moist feeling) can be provided.

The emulsion composition of the present invention is suited for producing, for example, cosmetics such as toilet lotion, milky lotion, cream, and gel, or an agent for skin external use.

The present invention provides:

[1] An emulsion composition comprising the following ingredients (A), (B), (C), (D), (E), and (F):

(A) a glyceryl monofatty acid ester derived from a linear-chain fatty acid having 10 to 24 carbon atoms,
(B) a higher alcohol having 10 to 24 carbon atoms,
(C) a ceramide,
(D) an anionic surfactant,
(E) a polar oil selected from branched fatty acid esters having an IOB of from 0.2 to 0.85 and having a hydroxyl group or an amino group, and
(F) water,
wherein the mass ratio, ((A)+(B)+(C)+(D))/(E), of the total content of ingredients (A), (B), and (C) and ingredient (D) in terms of acid to the content of ingredient (E) is from 1.2 to 25.

Further, in the present invention, the following compositions and production methods are preferred:

[2] The emulsion composition according to item [1], wherein ingredient (E) is a polar oil derived from a branched fatty acid selected from branched, fatty acid esters having hydroxyl groups and branched fatty acid esters having amino groups and is one or more branched fatty acid esters selected from octyldodecyl lactate, isostearic acid/myristic acid glyceryl, diglyceryl diisostearate, and di(cholesteryl/octyldodecyl) N-lauroyl-L-glutamate;

[3] The emulsion composition according to item [1] or [2], wherein the mass ratio of the content of ingredient (D) in terms of acid to the content of ingredient (E), (D)/(E), is from 0.1 to 5, preferably from 0.15 to 4, and more preferably from 0.2 to 3;

[4] The emulsion composition according to any one of items [1] to [3] further comprising a polyol (G) having an IOB of from 1.5 to 3.5;

[5] The emulsion composition according to any one of items [1] to [4] further comprising an oil other than ingredients (B), (C), and (E);

[6] The emulsion composition according to any one of items [1] to [5], wherein the mass ratio of the total content of ingredients (A), (B), and (C) and ingredient (D) in terms of acid to the content of ingredient (E), ((A)+(B)+(C)+(D))/(E), is from 1.25 to 20 and preferably from 1.5 to 17;

[7] The emulsion composition according to any one of items [1] to [6], wherein the mass ratio of ingredient (B) to ingredient (C), (B)/(C), is from 0.2 to 5, preferably from 0.25 to 4, and more preferably from 0.3 to 4;

[8] The emulsion composition according to any one of items [1] to [7], wherein the content of ingredient (A) is from 0.001% to 10% by mass, preferably from 0.05% to 3% by mass, and more preferably from 0.1% to 2% by mass;

[9] The emulsion composition according to any one of items [1] to [8], wherein the content of ingredient (B) is from 0.001% to 10% by mass, preferably from 0.1% to 3% by mass, and more preferably from 0.5% to 2.5% by mass;

[10] The emulsion composition according to any one of items [1] to [9], wherein the content of ingredient (C) is from 0.001% to 10% by mass, preferably from 0.1% to 5% by mass, and more preferably from 0.2% to 3% by mass;

[11] The emulsion composition according to any one of items [1] to [10], wherein the content of ingredient (D) in terms of acid is from 0.01% to 3% by mass, preferably from 0.05% to 2% by mass, and more preferably from 0.1% to 1.5% by mass;

[12] The emulsion composition according to any one of items [1] to [11], wherein the content of ingredient (E) is from 0.001% to 5% by mass, preferably from 0.15% to 4% by mass, and more preferably from 0.2% to 3% by mass;

[13] The emulsion composition according to any one of items [1] to [12], wherein the content of ingredient (F) is from 20% to 99% by mass and preferably from 40% to 90% by mass;

[14] The emulsion composition according to any one of items [4] to [13], wherein the content of ingredient (G) is from 0.001% to 20% by mass, preferably from 0.2% to 20% by mass, more preferably from 2% to 20% by mass, preferably from 0.2% to 15% by mass, and more preferably 2% to 10% by mass;

[15] The emulsion composition according to any one of items [1] to [14], wherein the mass ratio of the total content of ingredients (A), (B), and (C) and ingredient (D) in terms of acid to the content of ingredient (G), ((A)+(B)+(C)+(D))/(G), is from 0.1 to 20, preferably from 0.2 to 15, and more preferably from 0.22 to 3;

[16] The emulsion composition according to any one of items [1] to [15], wherein ingredient (D) is a sodium salt or an arginine salt of an acid selected from fatty acids having 12 to 24 carbon atoms, fatty acid amidosulfonic acids derived from fatty acids having 14 to 22 carbon atoms, polyoxyethylene alkyl ether phosphoric acids having C14-C22 alkyl groups, and N-acylglutamic acids derived from fatty acids having 12 to 22 carbon atoms; preferably a sodium salt or an arginine salt of an acid selected from fatty acid amidosulfonic acids derived from fatty acids having 18 to 22 carbon atoms, polyoxyethylene alkyl ether phosphoric acids having C18-C22 alkyl groups, and N-acylglutamic acids derived from fatty acids having 18 to 22 carbon atoms; and more preferably one or more selected from sodium N-stearoyl-N-methyltaurate, arginine N-stearoyl-L-glutamate, and sodium polyoxyethylene stearyl ether phosphate;

[17] The emulsion composition according to any one of items [1] to [16], wherein ingredient (A) is a glycerin fatty acid ester derived from a linear-chain fatty acid having 18 to 22 carbon atoms and preferably one or more selected from glyceryl monopalmitate, glyceryl monostearate, and glyceryl monobehenate;

[18] The emulsion composition according to any one of items [1] to [17], wherein ingredient (B) is a higher alcohol having 14 to 22 carbon atoms and preferably one or more selected from cetanol, stearyl alcohol, and behenyl alcohol;

[19] The emulsion composition according to any one of items [1] to [18], wherein ingredient (C) is a ceramide selected from a natural-type ceramide selected from ceramide Types 1 to 7 obtained by amidation of sphingosine, dihydrosphingosine, phytosphingosine, or sphingadienine and N-alkyl forms thereof, and a pseudo-ceramide represented by formula (2):

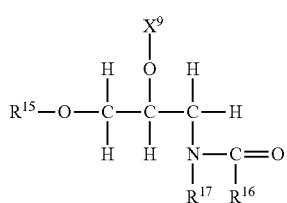

(2)

(wherein $R^{15}$ represents a C10 to C22 linear-chain, branched-chain, or cyclic, and saturated or unsaturated hydrocarbon group which is optionally substituted by a hydroxyl group or a hydrogen atom; $X^9$ represents a hydrogen atom, an acetyl group, or a glyceryl group; $R^{16}$ represents a C5 to C22 linear-chain, branched-chain, or cyclic, and saturated or unsaturated hydrocarbon group which is optionally substituted by a hydroxyl group or an amino group, or such a hydrocarbon group to which a C8 to C22 linear-chain or branched-chain and saturated or unsaturated fatty acid which is optionally substituted by a hydroxyl group is bonded at the ω-end via ester bonding; and $R^{17}$ represents a hydrogen atom or an alkyl group optionally substituted by a hydroxyl group, a hydroxyalkoxy group, an alkoxy group, or an acetoxy group and containing 1 to 30 carbon atoms in total).

[20] The emulsion composition according to any one of items of [1] to [19], wherein ingredient (G) is a polyol selected from 1,3-butylene glycol, isoprene glycol, propylene glycol, 1,3-propanediol, dipropylene glycol, diethylene glycol monoethyl ether, polypropylene glycol having a molecular weight of from 100 to 10000, polyethylene glycol having a molecular weight of from 100 to 10000, and polyoxyethylene diglyceryl ether having an average addition molar number of the oxyethylene of from 4 to 20;

[21] The emulsion composition according to any one of items [1] to [20], wherein the content of the oil having an IOB of from 0.1 to 0.2 other than ingredient (E) is 5% by mass or less;

[22] The emulsion composition according to any one of items [1] to [21] being an O/W emulsion composition;

[23] A method of producing the emulsion composition according to any one of items [1] to [22], the method comprising a step of heating and mixing ingredients (A) to (D) before a step of addition and mixing of ingredient (E);

[24] The method of producing the emulsion composition according to item [23], comprising a step of neutralizing the acid compound of ingredient (D) with a base before the step of addition and mixing of ingredient (E);

[25] A method of producing the emulsion composition according to any one of items [1] to [22], the method comprising a step of heating and stirring a first oil phase containing ingredients (A), (B), and (C) and the acid compound of ingredient (D) for mixing them and a step of heating a first water phase containing a base for neutralizing ingredient (D) and a part of water as ingredient (F) and adding the first water Phase to the first oil phase and mixing them;

[26] The method of producing the emulsion composition according to item [25], the method comprising a step of heating ingredient (E) and oily ingredients other than the first oil phase and further adding and mixing;

[27] A use of the emulsion composition according to any one of items [1] to [22] for skin application; and

[28] A use of the emulsion composition according to any one of items [1] to [22] for producing skin liniment.

EXAMPLES

Examples 1 to 5 and Comparative Examples 1 and 2

Oil-in-water emulsion compositions having formulations shown in Table 1 were produced and were evaluated for stability and feeling in use (frictionless feeling, moist feeling, and nonstickiness feeling). The results are also shown in Table 1.

In the compositions prepared in Examples, crystals of the ceramide were not or hardly observed by optical microscopic observation to show that the compositions were stable, and α-gel was confirmed by wide-angle X-ray diffraction analysis.

Producing Process

Ingredients of a first oil phase (mixture containing ingredients (A) to (C)) were heated and mixed at 80° C. to 90° C. To the first oil phase added were a first water phase (aqueous solution containing ingredient (D) and a part of ingredient (F)) heated to 80° C. to 90° C. and then a second oil phase (ingredient (E) and other oily ingredients) heated to 80° C. to 90° C. under propeller-stirring (300 rpm). The mixture was stirred with a homogenizer (7000 rpm) and was then cooled to 25° C. under propeller-stirring (300 rpm), followed by addition of a second water phase (the remaining ingredient (F) and other water-soluble ingredients) thereto. Thus, an O/W emulsion composition was prepared.

Evaluation Method (1) Stability:

Emulsion compositions of Examples and Comparative Examples were subjected to an accelerated storage test. The accelerated storage test is a cycle test of changing the storage temperature in a range of 15° C. to 60° C. in a day (a cycle of 15° C. to 60° C./day) and was continued for 7 days. The emulsion compositions of Examples and Comparative Examples after the accelerated storage test were subjected to optical microscopic observation under polarized light for investigating whether crystals were present or absent. The presence or absence of crystals was evaluated by the following criteria:

AA: No crystals were observed.
A: Crystals were slightly observed.
B: Small crystals were observed.
C: Needle crystals were observed.

(2) Feeling in Use (Frictionless Feeling, Moist Feeling, and Nonstickiness Feeling):

Each expert panelist applied 0.5 to 0.6 g of each emulsion composition to the face by sliding the fingers and evaluated the compositions according to the following four-stage criteria. The evaluation results are shown by the total value of the evaluation results of three expert panelists.

"Frictionless feeling" was evaluated from during the application to immediately after the application:
- 4: No friction was felt.
- 3: Friction was hardly felt.
- 2: Friction was slightly felt.
- 1: Friction was felt.

"Moist feeling" and "nonstickiness feeling" were evaluated at the application and for 3 min. from immediately after the application:
- 4: Satisfactory.
- 3: Moderately satisfactory.
- 2: Slightly satisfactory.
- 1: Not satisfactory.

TABLE 1

|  |  |  | Example | | | | | Comparative Example | |
|---|---|---|---|---|---|---|---|---|---|
|  |  |  | 1 | 2 | 3 | 4 | 5 | 1 | 2 |
| Ingredient (% by mass) | A | Glyceryl monobehenate | 1 | 1 | 1 | 1 | 1 | 1 | 1 |
|  | B | Cetanol | 1 | 1 | 1 | 1 | 1 | 1 | 1 |
|  | C | N-(Hexadecyloxyhydroxypropyl)-N-hydroxyethyl hexadecanamide | 2 | 2 | 2 | 2 | 2 | 2 | 2 |
|  | D | N-Stearoyl-L-glutamic acid | 0.6 | 0.6 | 0.6 | 0.6 | 0.6 | 0.6 | 0.6 |
|  |  | L-Arginine | 0.4 | 0.4 | 0.4 | 0.4 | 0.4 | 0.4 | 0.4 |
|  | E | Isostearic add/mytistic acid glyceryl (IOB = 0.32) | 0.2 | 1 | 2 | 3 | 4 | 0.1 | 7.5 |
|  | F | Water | balance | balance | balance | balance | balance | balance | balance |
|  |  | Total | 100 | 100 | 100 | 100 | 100 | 100 | 100 |
| Mass ratio |  | $((A) + (B) + (C) + (D)^{*1})/(E)$ | 23.0 | 4.6 | 2.3 | 1.5 | 1.2 | 46.0 | 06 |
|  |  | $(D)^{*1}/(E)$ | 3.0 | 0.6 | 0.3 | 0.2 | 0.2 | 6.0 | 0.1 |
| Evaluation |  | Stability | AA | AA | A | A | B | AA | C |
|  |  | Feeling in use: Frictionless feeling | 8 | 9 | 9 | 12 | 12 | 3 | 12 |
|  |  | Moist feeling | 9 | 9 | 9 | 9 | 9 | 6 | 12 |
|  |  | Nonstickiness feeling | 9 | 9 | 9 | 9 | 9 | 12 | 6 |

*[1] the content of ingredient (D) is that in terms of acid.

Examples 6 to 13

O/W emulsion compositions having formulations shown in Table 2 were produced as in Examples 1 to 5 and were evaluated for stability and feeling in use (frictionless feeling, most feeling, and nonstickiness feeling). The results are also shown in Table 2.

In the compositions prepared in Examples, crystals of the ceramide were not or hardly observed by optical electromicroscopic observation to show that the compositions were stable, and α-gel was confirmed by wide-angle X-ray diffraction analysis,

TABLE 2

|  |  |  | Example | | | | | | | |
|---|---|---|---|---|---|---|---|---|---|---|
|  |  |  | 6 | 7 | 8 | 9 | 10 | 11 | 12 | 13 |
| Ingredient (% by mass) | A | Glyceryl monobehenate | 1 | 1 | 1 | 1 | 1 |  | 1 | 1 |
|  | A | Glyceryl monomyristate |  |  |  |  |  | 1 |  |  |
|  | B | Behenyl alcohol |  |  |  |  |  | 1 |  |  |
|  | B | Cetanol | 1 | 1 | 1 | 1 |  |  | 2.4 | 0.6 |
|  | B | Myristyl alcohol |  |  |  |  | 1 |  |  |  |
|  | C | N-(Hexadecyloxyhydroxypropyl)-N-hydroxyethyl hexadecanamide | 2 | 2 | 2 | 2 | 2 | 2 | 0.6 | 2.4 |
|  | D | N-Stearoyl-L-glutamic acid | 0.3 | 0.6 | 1.2 | 0.6 | 0.6 | 0.6 | 0.6 | 0.6 |
|  |  | L-Arginine | 0.2 | 0.4 | 0.8 | 0.4 | 0.4 | 0.4 | 0.4 | 0.4 |
|  | E | Isostearic acid/myristic acid glyceryl IOB = 0.32 | 2 | 2 | 2 | 0.2 | 2 | 2 | 2 | 2 |
|  | F | Water | balance | balance | balance | balance | balance | balance | balance | balance |
|  |  | Total | 100 | 100 | 100 | 100 | 100 | 100 | 100 | 100 |
| Mass ratio |  | $((A) + (B) + (C) + (D)^{*1})/(E)$ | 2.2 | 2.3 | 2.6 | 23.0 | 2.3 | 2.3 | 2.3 | 2.3 |
|  |  | $(D)^{*1}/(E)$ | 0.2 | 0.3 | 0.6 | 3.0 | 0.3 | 0.3 | 0.3 | 0.3 |
| Evaluation |  | Stability | A | A | A | AA | A | A | A | AA |
|  |  | Feeling in use: Frictionless feeling | 6 | 10 | 9 | 8 | 9 | 9 | 11 | 6 |
|  |  | Moist feeling | 9 | 9 | 9 | 9 | 9 | 9 | 9 | 9 |
|  |  | Nonstickiness feeling | 12 | 9 | 9 | 9 | 9 | 9 | 9 | 12 |

*[1] the content of ingredient (D) is that in terms of acid.

Examples 14 to 20 and Comparative Examples 3 and 4

Oil-in-water emulsion compositions having formulations shown in Table 3 were produced as in Examples 1 to 5 and were evaluated for stability and feeling in use (frictionless feeling, moist feeling, and nonstickiness feeling). The results are also shown in Table 3.

In the compositions prepared in Examples, crystals of the ceramide were not or hardly observed by optical electromicroscopic observation to show that the compositions were stable, and α-gel was confirmed by wide-angle X-ray diffraction analysis.

TABLE 3

| | | | Example | | | | | | | Comparative Example | |
|---|---|---|---|---|---|---|---|---|---|---|---|
| | | | 14 | 15 | 16 | 17 | 18 | 19 | 20 | 3 | 4 |
| Ingredient (% by mass) | A | Glyceryl monobehenate | 1 | 1 | 1 | 1 | 1 | 1 | 1 | 1 | 1 |
| | B | Cetanol | 1 | 1 | 1 | 1 | 1 | 1 | 1 | 1 | 1 |
| | C | N-(Hexadecyloxyhydroxypropyl)-N hydroxyethyl hexadecanamide | 2 | 2 | 2 | 2 | 2 | 2 | 2 | 2 | 2 |
| | D | N-Stearoyl-L-glutamic acid | 0.6 | 0.6 | 0.6 | 0.6 | 0.6 | 0.6 | 0.6 | 0.6 | 0.6 |
| | | L-Arginine | 0.4 | 0.4 | 0.4 | 0.4 | 0.4 | 0.4 | 0.4 | 0.4 | 0.4 |
| | E | Di(cholesteryl/octyldodecyl) N-lauroyl-L-glutamate (IOB = 0.29 to 0.35) | 2.5 | | | | | | | | |
| | | Octyldodecyl lactate (IOB = 0.36) | | 2.5 | 1.5 | | | | | | |
| | | Isostearic acid/myristic acid glyceryl (IOB = 0.32) | | | 1 | 2.5 | | | | | |
| | | Diglyceryl diisostearate (IOB = 0.42) | | | | | 2.5 | | | | |
| | | Erythrityl triethylhexanoate (IOB = 0.55) | | | | | | 2.5 | | | |
| | | Diglyceryl monoisostearate (IOB = 0.81) | | | | | | | 2.5 | | |
| | | Isopropyl palmitate (IOB = 0.162) | | | | | | | | | 2.5 |
| | | Hydrogenated polyisobutene | | | | | | | | 2.5 | |
| | F | Water | balance | balance | balance | balance | balance | balance | balance | balance | balance |
| | | Total | 100 | 100 | 100 | 100 | 100 | 100 | 100 | 100 | 100 |
| Mass ratio | | ((A) + (B) + (C) + (D)*¹)/(E) | 1.8 | 1.8 | 1.0 | 1.8 | 1.8 | 1.8 | 1.8 | — | — |
| | | (D)*¹/(E) | 0.2 | 0.2 | 0.2 | 0.2 | 0.2 | 0.2 | 0.2 | — | — |
| Evaluation | | Stability | B | A | A | A | A | A | A | A | A |
| | | Feeling in use: Frictionless feeling | 9 | 8 | 12 | 8 | 9 | 9 | 9 | 3 | 4 |
| | | Moist feeling | 12 | 12 | 12 | 12 | 12 | 12 | 12 | 6 | 7 |
| | | Nonstickiness feeling | 9 | 9 | 9 | 9 | 9 | 9 | 9 | 12 | 11 |

*¹the content of ingredient (D) is that in terms of acid.

Examples 21 to 31

Oil-in-water emulsion compositions having formulations shown in Table 4 were produced as in Examples 1 to 5 and were evaluated for stability and feeling in use (frictionless feeling, moist feeling, and nonstickiness feeling). The results are also shown in Table 4.

In the compositions prepared in Examples, crystals of the ceramide were hardly observed by optical electromicroscopic observation to show that the compositions were stable, and α-gel was confirmed by wide-angle X-ray diffraction analysis.

TABLE 4

| | | | Example | | | | | | | | | | |
|---|---|---|---|---|---|---|---|---|---|---|---|---|---|
| | | | 21 | 22 | 23 | 24 | 25 | 26 | 27 | 28 | 29 | 30 | 31 |
| Ingredient (% by mass) | A | Glyceryl monobehenate | 1 | 1 | 1 | 1 | 1 | 1 | 1 | 1 | 1 | 1 | 1 |
| | B | Cetanol | 1 | 1 | 1 | 1 | 1 | 1 | 1 | 1 | 1 | 1 | 1 |
| | C | N-(Hexadecyloxyhydroxypropyl)-N-hydroxyethyl hexadecanamide | 2 | 2 | 2 | 2 | 2 | 2 | 2 | 2 | 2 | 2 | 2 |
| | D | N-Stearoyl-L-glutamic acid | 0.6 | 0.6 | 0.6 | 0.6 | 0.6 | 0.6 | 0.6 | 0.6 | 0.6 | 0.6 | 0.6 |
| | | L-Arginine | 0.4 | 0.4 | 0.4 | 0.4 | 0.4 | 0.4 | 0.4 | 0.4 | 0.4 | 0.4 | 0.4 |
| | E | Diglyceryl diisostearate (IOB = 0.42) | 0.3 | 0.3 | 0.3 | 0.3 | 0.3 | 0.3 | 0.3 | 0.3 | 0.3 | 0.3 | 0.3 |
| | G | 1,3-Butylene glycol (IOB = 2.50) | 0.3 | 2.5 | 5 | 10 | 20 | | | | 5 | 5 | 5 |
| | | Dipropylene glycol (IOB = 1.83) | | | | | | 5 | | | | | |
| | | Propylene glycol (IOB = 3.33) | | | | | | | 5 | | | | |
| | | 1,3-Propanediol (IOB = 3.33) | | | | | | | | 5 | | | |
| | | Hydrogenated polydecene | | | | | | | | | 2.5 | | |
| | | Hydrogenated polyisobutene | | | | | | | | | | 2.5 | |
| | | Olive oil | | | | | | | | | | | 2.5 |
| | F | Water | balance | balance | balance | balance | balance | balance | balance | balance | balance | balance | balance |
| | | Total | 100 | 100 | 100 | 100 | 100 | 100 | 100 | 100 | 100 | 100 | 100 |

TABLE 4-continued

| | | Example | | | | | | | | | | |
|---|---|---|---|---|---|---|---|---|---|---|---|---|
| | | 21 | 22 | 23 | 24 | 25 | 26 | 27 | 28 | 29 | 30 | 31 |
| Mass ratio | ((A) + (B) + (C) + (D)*¹)/(E) | 15.3 | 15.3 | 15.3 | 15.3 | 15.3 | 15.3 | 15.3 | 15.3 | 15.3 | 15.3 | 15.3 |
| | (D)*¹/(E) | 2.0 | 2.0 | 2.0 | 2.0 | 2.0 | 2.0 | 2.0 | 2.0 | 2.0 | 2.0 | 2.0 |
| Evaluation | Stability | A | A | A | A | A | A | A | A | A | A | A |
| | Feeling in use: Frictionless feeling | 9 | 9 | 12 | 12 | 11 | 12 | 12 | 12 | 12 | 12 | 12 |
| | Moist feeling | 9 | 9 | 12 | 12 | 12 | 12 | 12 | 12 | 12 | 12 | 12 |
| | Nonstickiness feeling | 12 | 12 | 9 | 9 | 6 | 9 | 9 | 9 | 12 | 12 | 12 |

*¹the content of ingredient (D) is that in terms of acid.

Examples 32 to 34

Oil-in-water emulsion compositions of Example 32 shown in Table 5 and Examples 33 and 34 shown in Table 6 were produced as in Examples 1 to 5. In the resulting compositions, α-gel was confirmed by wide-angle X-ray diffraction analysis, and the ceramide was hardly crystallized and was stably contained. Thus, the compositions had high moisturizing effects, reduced friction feeling, and excellent feeling in use.

TABLE 5

| Example 32 | |
|---|---|
| Ingredient | (% by mass) |
| N-(Hexadecyloxyhydroxypropyl)-N-hydroxyethyl hexadecanamide | 2 |
| Cetanol | 1 |
| Glyceryl monobehenate | 1 |
| N-Stearoyl-L-glutamic acid | 0.6 |
| L-Arginine | 0.4 |
| Purified water | 64.18 |
| Squalane | 3 |
| Diglyceryl diisostearate (IOB = 0.42) | 0.5 |
| Methyl polysiloxane | 4 |
| Methyl polysiloxane/cross-linked methyl polysiloxane mixture | 0.5 |
| Glyceryl | 15 |
| 1,3-Butylene glycol | 5 |
| Carboxy vinyl polymer | 0.2 |
| Xanthan gum | 0.1 |
| Potassium hydroxide | 0.1 |
| Eucalyptus extract | 0.2 |
| Water-soluble ginger extract (K) | 0.2 |
| False-arborvitae tree extract | 0.2 |
| Horse chestnut extract | 6.2 |
| Chamomilla recutita extract | 0.2 |
| Japanese citron (Yuzu) extract | 0.2 |
| Clove extract | 0.2 |
| Althaea officinalis extract | 0.2 |
| Tea extract | 0.2 |
| Brown algae extract | 0.2 |
| Methyl paraoxybenzoate | 0.4 |
| Perfume | 0.02 |
| Total | 100.00 |
| Stability | AA |
| Feeling in use: Frictionless feeling | 12 |
| Moist feeling | 12 |
| Nonstickiness feeling | 12 |

TABLE 6

| | | | Example | |
|---|---|---|---|---|
| | | | 33 | 34 |
| Ingredient (% by mass) | C | N-(Hexadecyloxyhydroxypropyl)-N-hydroxyethyl hexadecanamide | 0.30 | 1.80 |
| | B | Cetanol | 0.15 | 0.60 |
| | A | Glyceryl monobehenate | 0.20 | 1.80 |

TABLE 6-continued

| | | | Example | |
|---|---|---|---|---|
| | | | 33 | 34 |
| | D | N-Stearoyl-L-glutamic acid | 0.10 | 0.58 |
| | | L-Arginine | 0.05 | 0.32 |
| | | Squalane | 1 | 5 |
| | | Methyl polysiloxane | 5 | 5 |
| | E | Diglyceryl diisostearate (IOB = 0.42) | 0.2 | 1 |
| | | Glyceryl | 10 | 20 |
| | G | 1,3-Butylene glycol | 3 | 5 |
| | | Carboxyvinyl polymer | 0.1 | 0.1 |
| | | Potassium hydroxide | 0.05 | 0.05 |
| | | Methyl paraoxybenzoate | 0.3 | 0.4 |
| | | Perfume | 0.02 | 0.02 |
| | F | Purified water | balance | balance |
| | | Total | 100 | 100 |
| Mass ratio | | ((A) + (B) + (C) + (D)*¹)/(E) | 3.7 | 4.8 |
| | | (D)*¹/(E) | 0.5 | 0.6 |
| Evaluation | | Feeling in use: Frictionless feeling | 12 | 12 |
| | | Moist feeling | 12 | 12 |
| | | Nonstickiness feeling | 12 | 8 |

*¹the content of ingredient (D) is that in terms of acid.

Examples 35 to 37

Oil-in-water emulsion compositions of Examples 35 to 37 shown in Table 7 were produced as in Examples 1 to 5. In the resulting O/W emulsion compositions, α-gel was confirmed by wide-angle X-ray diffraction analysis, and the ceramide was hardly crystallized and was stably contained. Thus, the compositions had high moisturizing effects, reduced friction feeling, and excellent feeling in use.

TABLE 7

| | | | Example | | |
|---|---|---|---|---|---|
| | | Ingredient (% by mass) | 35 | 36 | 37 |
| | C | N-(Hexadecyloxyhydroxypropyl)-N-hydroxyethyl hexadecanamide | 2 | 2 | 2 |
| | B | Cetanol | 1 | 1 | 1 |
| | A | Glyceryl monobehenate | 1 | 1 | 1 |
| | D | N-Stearoyl-L-glutamic acid | 0.6 | | |
| | | L-Arginine | 0.4 | | |
| | D | Sodium N-stearoyl-N-methyltaurate | | 0.6 | |
| | D | Sodium polyoxyethylene lauryl ether phosphate | | | 0.5 |
| | E | Diglyceryl diisostearate (IOB = 0.42) | 0.5 | 0.5 | 0.5 |
| | | Purified water | 64.68 | 65.08 | 65.18 |
| | | Squalane | 3 | 3 | 3 |
| | | Methyl polysiloxane | 4 | 4 | 4 |
| | | Glyceryl | 15 | 15 | 15 |
| | G | 1,3-Butylene glycol | 5 | 5 | 5 |
| | | Carboxyvinyl polymer | 0.2 | 0.2 | 0.2 |

TABLE 7-continued

| | Example | | |
|---|---|---|---|
| Ingredient (% by mass) | 35 | 36 | 37 |
| Xanthan gum | 0.1 | 0.1 | 0.1 |
| Potassium hydroxide | 0.1 | 0.1 | 0.1 |
| *Eucalyptus* extract | 0.2 | 0.2 | 0.2 |
| Water-soluble ginger extract (K) | 0.2 | 0.2 | 0.2 |
| False-arborvitae tree extract | 0.2 | 0.2 | 0.2 |
| Horse chestnut extract | 0.2 | 0.2 | 0.2 |
| Chamomilla recutita extract | 0.2 | 0.2 | 0.2 |
| Japanese citron (Yuzu) extract | 0.2 | 0.2 | 0.2 |
| Clove extract | 0.2 | 0.2 | 0.2 |
| *Althaea officinalis* extract | 0.2 | 0.2 | 0.2 |
| Tea extract | 0.2 | 6.2 | 0.2 |
| Brown algae extract | 0.2 | 0.2 | 0.2 |
| Methyl paraoxybenzoate | 0.4 | 0.4 | 0.4 |
| Perfume | 0.02 | 0.02 | 0.02 |
| Total | 100 | 100 | 100 |

Examples 38 to 40

Oil-in-water emulsion compositions of Examples 38 to 40 shown in Table 8 were produced as in Examples 1 to 5. In the resulting O/W emulsion compositions, α-gel was confirmed by wide-angle X-ray diffraction analysis, and the ceramide was hardly crystallized and was stably contained. Thus, the compositions had high moisturizing, effects, reduced friction feeling, and excellent feeling in use.

TABLE 8

| | | | Example | | |
|---|---|---|---|---|---|
| | | Ingredient (% by mass) | 38 | 39 | 40 |
| Ingre- | A | Glyceryl monostearate | 0.07 | | |
| dient | A | Glyceryl monobehenate | | 1.50 | 2.50 |
| (% by | B | Cetanol | 0.1 | 1.50 | 1.00 |
| mass) | C | N-(Hexadecyloxyhydroxy-propyl)-N-hydroxyethyl hexadecanamide | | 4.00 | 1.00 |
| | | Ceramide 2 | 0.1 | | |
| | D | N-Stearoyl-L-glutamic acid | 0.05 | 1.20 | 0.60 |
| | | L-Arginine | 0.03 | 0.80 | 0.40 |
| | E | Diglyceryl diisostearate (IOB = 0.42) | 0.15 | 5 | 1 |
| | F | Water | balance | balance | balance |
| | | Squalane | | 5 | 5 |
| | | Methyl polysiloxane | 5.00 | 5 | 5 |
| | | Glyceryl (86%) | 10.00 | 10 | 10 |
| | G | 1,3-Butylene glycol | 10.00 | 10 | 10 |
| | | Carboxyvinyl polymer | 0.10 | 0.1 | 0.1 |
| | | Potassium hydroxide | 0.05 | 0.05 | 0.05 |
| | | Methyl paraoxybenzoate | 0.3 | 0.3 | 0.3 |
| | | Perfume | 0.02 | 0.02 | 0.02 |
| | | Total | 100 | 100 | 100 |
| Mass | | ((A) + (B) + (C) + (D)*1)/(E) | 2.1 | 1.6 | 5.1 |
| ratio | | (D)*1/(E) | 0.3 | 0.2 | 0.6 |
| Evalua- | | Feeling in use: Frictionless feeling | 12 | 12 | 12 |
| tion | | Moist feeling | 8 | 12 | 11 |
| | | Nonstickiness feeling | 8 | 10 | 11 |

*1 the content of ingredient (D) is that in terms of acid.

What is claimed is:

1. An emulsion composition comprising the following ingredients:
   (A) a glyceryl monofatty acid ester derived from a linear-chain fatty acid having 10 to 24 carbon atoms,
   (B) a higher alcohol having 10 to 24 carbon atoms,
   (C) a ceramide,
   (D) a anionic surfactant,
   (E) a polar oil selected from at least one of octyldodecyl lactate, difatty acid glyceryl ester composed of isostearic acid and myristic acid, diglyceryl diisostearate and di(cholesteryl/octyldodecyl)N-lauroyl-L-glutamate,
   (F) water, and
   an oil having an IOB of from 0.1 to 0.2 that is other than ingredient (B), (C) and (E), wherein the oil having an IOB of from 0.1 to 02 that is other than ingredient (B), (C) and (E) comprises up to 5% by mass of the composition, wherein the mass ratio of the total content of ingredients (A), (B), and (C) and ingredient (D) in terms of acid to the content of ingredient (E), ((A)+(B)+(C)+(D))/(E), is from 1.2 to 25, and
   wherein the mass ratio of the content of ingredient (D) in terms of acid to the content of ingredient (E), (D)/(E), is from 0.1 to 5.

2. The emulsion composition according to claim 1, further comprising a polyol (G) having an IOB of from 1.5 to 3.5.

3. The emulsion composition according to claim 1, further comprising an oil other than ingredient (B), (C), and (E) and other than the oil having an IOB of from 0.1 to 0.2 that is other than ingredient (B), (C) and (E).

4. The emulsion composition according to claim 1, wherein ingredient (A) is at least one glyceryl monofatty acid ester selected from the group consisting of glyceryl monopalmitate, glyceryl monostearate, and glyceryl monobehenate.

5. The emulsion composition according to claim 1, wherein ingredient (B) is at least one higher alcohol selected from the group consisting of cetanol, stearyl alcohol, and behenyl alcohol.

6. The emulsion composition according to claim 1, wherein ingredient (C) is at least one ceramide selected from the group consisting of a natural-type ceramide selected from ceramide Types 1 to 7 obtained by amidation of sphingosine, dihydrosphingosine, phytosphingosine, or sphingadienine and N-alkyl forms thereof, and a pseudo-ceramide represented by formula (2):

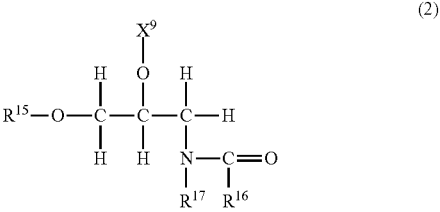

(2)

wherein $R^{15}$ represents a C10 to C22 linear-chain, branched-chain, or cyclic, and saturated or unsaturated hydrocarbon group which is optionally substituted by a hydroxyl group or represents a hydrogen atom;

$X^9$ represents a hydrogen atom, an acetyl group, or a glyceryl group;

$R^{16}$ represents a C5 to C22 linear-chain, branched-chain, or cyclic, and saturated or unsaturated hydrocarbon group which is optionally substituted by a hydroxyl group or an amino group, or such a hydrocarbon group to which a C8 to C22 linear-chain or branched-chain and saturated or unsaturated fatty acid which is optionally substituted by a hydroxyl group is bonded at the ω-end via ester bonding; and $R^{17}$ represents a hydrogen atom or an alkyl group optionally substituted by a hydroxyl group, a hydroxyalkoxy group, an alkoxy group, or an acetoxy group and containing 1 to 30 carbon atoms in total.

7. The emulsion composition according to claim 1, wherein ingredient (D) is at least one anionic surfactant selected from the group consisting of a sodium salt and an arginine salt of an acid selected from fatty acid amidosulfonic acids derived from fatty acids having 18 to 22 carbon atoms, polyoxyethylene alkyl ether phosphoric acids having C18-C22 alkyl groups, and N-acylglutamic acids derived from fatty acids having 18 to 22 carbon atoms.

8. The emulsion composition according to claim 1, wherein the mass ratio of the content of ingredient (B) to the content of ingredient (C), (B)/(C), is from 0.2 to 5.

9. The emulsion composition according to claim 2, wherein the mass ratio of the total content of ingredients (A), (B), and (C) and ingredient (D) in terms of acid to the content of ingredient (G), ((A)+(B)+(C)+(D))/(G), is from 0.1 to 20.

10. A method for using the emulsion composition according to claim 1, the method comprising applying it to the skin.

* * * * *